(12) United States Patent
Graham

(10) Patent No.: US 6,827,761 B2
(45) Date of Patent: Dec. 7, 2004

(54) PARTICLE CONCENTRATOR

(75) Inventor: Lisa A. Graham, Dunrobin (CA)

(73) Assignee: Her Majesty The Queen in Right of Canada as represented by the Minister of the Environment, Gloucester (CA)

( * ) Notice: Subject to any disclaimer, the term of this patent is extended or adjusted under 35 U.S.C. 154(b) by 0 days.

(21) Appl. No.: 10/363,295

(22) PCT Filed: Sep. 7, 2001

(86) PCT No.: PCT/CA01/01283

§ 371 (c)(1),
(2), (4) Date: Feb. 28, 2003

(87) PCT Pub. No.: WO02/21100

PCT Pub. Date: Mar. 14, 2002

(65) Prior Publication Data

US 2004/0011196 A1 Jan. 22, 2004

(30) Foreign Application Priority Data

Sep. 8, 2000 (CA) .............................................. 2317830

(51) Int. Cl.[7] ................................................ B03C 3/14
(52) U.S. Cl. ................................ 95/32; 55/462; 95/70; 95/78; 95/267; 96/55; 96/60; 96/96; 209/127.1; 209/131
(58) Field of Search .............................. 95/31, 32, 70, 95/78, 267; 96/55, 60, 95, 96; 55/462; 209/127.1, 131, 143

(56) References Cited

U.S. PATENT DOCUMENTS

| 3,059,772 A | 10/1962 | Le Baron | 209/127.1 |
|---|---|---|---|
| 3,496,701 A | 2/1970 | Berg | 95/80 |
| 3,853,750 A * | 12/1974 | Volsy | 209/127.1 |
| 4,023,398 A | 5/1977 | French et al. | 95/60 X |
| 4,301,002 A * | 11/1981 | Loo | 209/143 |
| 4,734,105 A | 3/1988 | Eliasson et al. | 95/62 |
| 4,767,524 A * | 8/1988 | Yeh et al. | 209/143 |
| 4,863,491 A * | 9/1989 | Brandt et al. | 95/29 |
| 4,972,957 A | 11/1990 | Liu et al. | 209/143 |
| 4,976,752 A * | 12/1990 | Torok et al. | 96/43 |
| 5,425,802 A * | 6/1995 | Burton et al. | 95/32 |
| 5,439,513 A | 8/1995 | Periasamy et al. | 96/25 |
| 5,447,553 A * | 9/1995 | Apffel et al. | 95/32 |
| 5,498,271 A * | 3/1996 | Marple et al. | 55/321 |
| 5,683,494 A | 11/1997 | Altman et al. | 96/55 |
| 5,762,691 A | 6/1998 | Gondar | 96/60 |
| 6,090,189 A * | 7/2000 | Wikstrom et al. | 96/69 |
| 6,163,098 A * | 12/2000 | Taylor et al. | 310/308 |
| 6,589,314 B1 * | 7/2003 | Page et al. | 95/32 |

FOREIGN PATENT DOCUMENTS

GB 794834 * 5/1958 ..................... 95/32

\* cited by examiner

*Primary Examiner*—Richard L. Chiesa
(74) *Attorney, Agent, or Firm*—McFadden, Fincham

(57) ABSTRACT

Particles in a fluid flow are concentrated by a combination of electrical charging and focussing and passage through a virtual impact concentrator. The fluid is passed through an electrical charging section and an electrical focussing section and then to a virtual impact concentrator. The majority of charged particles in a selected size range are collected through a minor discharge passage extending axially from the virtual impact concentrator. The invention is particularly suitable for sampling engine exhaust gases and ambient aerosols.

13 Claims, 7 Drawing Sheets

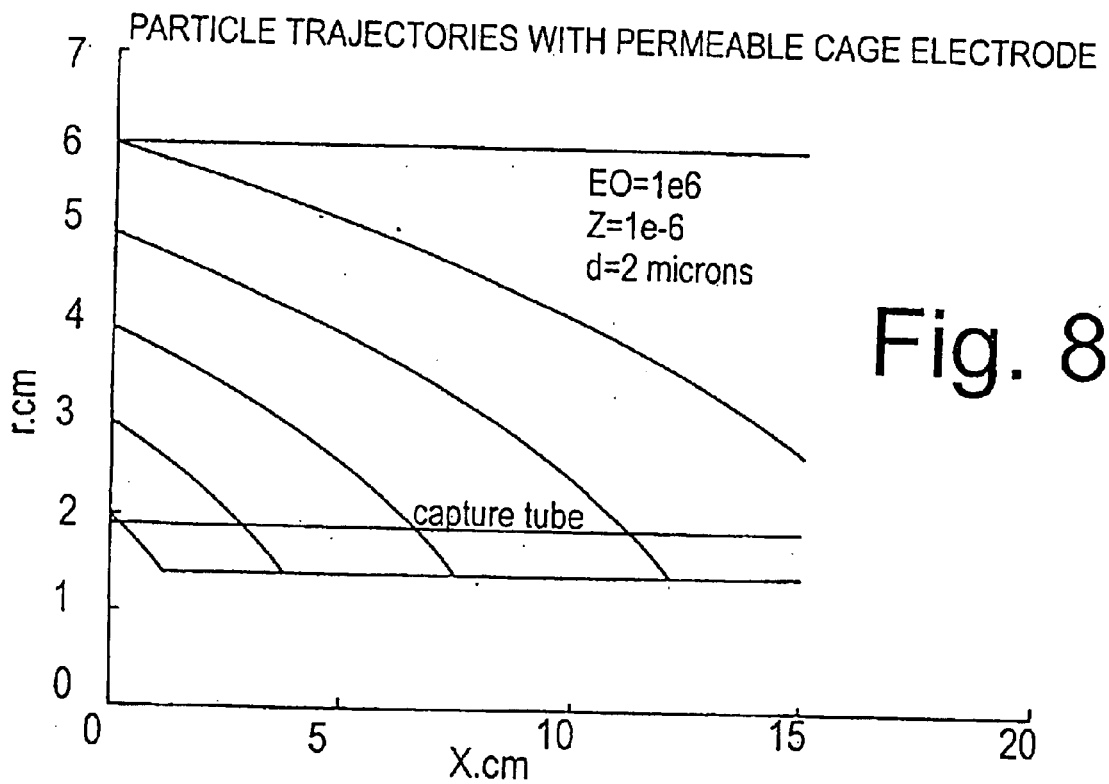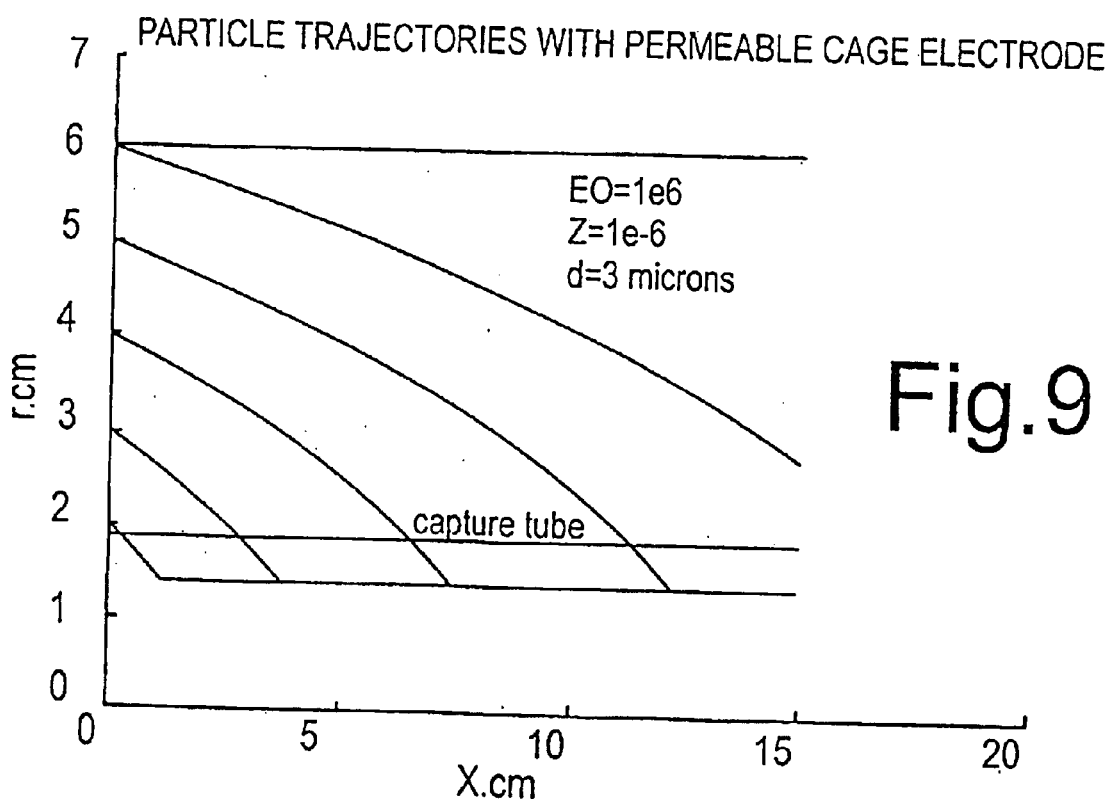

PARTICLE CONCENTRATOR

FIELD OF THE INVENTION

The invention relates sampling of pollutants such as for sampling gasoline and diesel emissions of engines or of ambient air. In particular, the invention relates to an apparatus to concentrate fine particles in a fluid flow, for collection, detection and/or measurement thereof, and in particular though not exclusively to the concentration of and collection of fine particulate material for chemical characterization of vehicle emissions or the like.

BACKGROUND OF THE INVENTION

For quality data to be obtained from chemical analysis of samples a significant amount of material is needed, ideally 50–100 mg. Using current sampling practices, a single atmospheric aerosol sample yields a sample size of about 300 $\mu$g, typical diesel emission samples are about 2 mg and typical light duty gasoline emissions samples are about 20 $\mu$g.

There are several approaches that can be taken for increasing the amount of material collected for analysis.

High volume sampling using large filters (8"×10") may lead to high blanks or background concentrations due to the large amount of filter media. Using smaller filters at the same high flow rate requires a greater pressure drop across the filter and a corresponding loss of volatile material from the sample.

Multiple filters can be used to collect samples at a lower flow rate but this offers the same risk of high blanks or background concentrations as high volume sampling. Multiple samples can be collected simultaneously, requiring multiple sets of sampling apparatus. If multiple samples are collected sequentially, then the sampled gas must be of a consistent composition, necessitating multiple repeats of a vehicle test or an atmosphere that is not changing.

Particle concentrators such as virtual impact-type concentrators have been used in the past for inhalation exposure studies.
1. Sioutas et al. in Environmental Health Perspectives, 103, 2, 172–177, 1995
2. Sioutas et al. in Inhalation Toxicology, 7, 633–644, 1995
3. Sioutas et al. in J. Aerosol Sci., 28, 6, 1057–1071, 1977

These devices can achieve a 10–50 fold increase in particle concentration without changing the composition of the matrix gas. There are two particle size cut-offs on these concentrators. The upper size limit is imposed by a preselection stage that allows only particles of a given size or smaller to pass into the concentrator. The lower size limit is imposed by the design constraints of the concentrator itself: the aerodynamics and geometry of the virtual impactors used in the particle concentrator impose the lower size limit. Typically, the upper size cut is 10 $\mu$m to 2.5 $\mu$m and the lower size cut is 0.1 to 0.15 $\mu$m diameter. Some work has been done in collecting samples for chemical analysis using these concentrators.

The particle concentrators used for inhalation studies are designed specifically for that purpose and are based on the observation that 90% or more of the mass of inhalable ambient aerosol is accounted for by particles in the range of 0.1 to 2.5 $\mu$m diameter. The situation is different for mobile source emissions samples where most of the mass is accounted for by particles in the range of 0.05 to 0.2 $\mu$m diameter and most particles are less than 0.1 $\mu$m in diameter.

Several approaches have been used successfully for collecting samples of smaller particles with impactors. The MOUDI™ and ELPI™ devices are cascade impactors which rely on a very large pressure drop across the device to obtain mass distribution information on particles between 0.03 to 10 $\mu$m diameter. These devices operate at relatively low sampling rates so collection of sufficient material for chemical analysis requires either multiple samples or long duration sampling. The large pressure drop also results in loss of volatile material from the sample.

The ELPI instrument charges particles and passes the sample stream containing the charged particles through a cascade impactor. As the particles impact on the stage of the impactor corresponding to their size, the electric current produced is measured, giving real time particle size distribution data on the sample stream. The lowest stage of the ELPI system detects particles down to 0.03 $\mu$m diameter and smaller. However, this arrangement does not rely on electrostatics for separation.

Considerable prior art exists in which electrostatic separation is used for various purposes. A typical example is Altman et al. U.S. Pat. No. 5,683,494, to a separator for use in cleansing factory discharges. The apparatus comprises a cyclonic type separator with an electrostatic charge imparted to the particles to enhance the cyclonic effect.

Additional prior art exists in which a "vertical virtual impactor" type of separation occurs. A typical example is Gondar U.S. Pat. No. 5,762,691, to a particulate collection system to purify air in the vicinity of a power tool. Air is drawn into a tube thereby forming a localized vacuum-induced aerodynamic fluid flow in the vicinity of the work piece. Particles are then precipitated by electrostatic forces.

Electrostatic separation arrangements are also known. A commercial particle sizing instrument using this approach is sold by TSI Incorporated—SMPS™.

The SMPS instrument pass particles with a Boltzan neutral charge distribution through a varying electric field. Only particles with a specific charge to mass ratio successfully traverse the electric field to be collected at the detector. This instrument also gives particle size distribution information, but not in real time as it takes approximately one minute to complete a size-range scan. The smallest size of particles that this instrument can measure is 0.007 $\mu$m diameter, approaching the division between molecule and particle.

SUMMARY AND OBJECTS OF THE INVENTION

An object of the invention is to provide an improved particle concentrator suitable for sampling of vehicle emissions and ambient air (or atmospheric aerosols). It is a further object to permit efficient sampling via a high concentration effect, while also permitting retention of even small particles.

The present invention provides for the combination of two known arrangements to provide an improved and more effective concentration and collection of fine particulate material. The invention relates to the combination of charging of particles and focussing by use of electric fields in combination with aerodynamics to achieve particle concentration in the gas flow which has not been done previously. The key difference is that the concentrated particles remain suspended in a gas flow and are not electrostatically collected or removed from the gas flow.

The various features of the present invention are:
the use of an aerodynamic particle concentrator to achieve concentration of particles in a gas stream;
the charging of the particles before they enter the particle concentrator; and the use of electric fields to draw the smallest particles (0.30 µm and smaller, and more preferably, 0.15 µm and smaller), which would otherwise escape concentration by the aerodynamic concentrator, into the concentrated flow.

A further feature is the potential decrease in particle loss to the walls due to collisions as the particles can be focussed away from the surfaces of the concentrator.

Various advantages occur from the invention, as follows:

The concentrator offers reductions in sampling time needed for collection of sufficient material for chemical analysis, thus reducing the cost of sample collection (reducing replicate sample collection or repeating of test sequences).

The concentrator offers the possibility of increased temporal or diurnal resolution of the analysis of samples collected of atmospheric aerosols. Currently, sufficient material is collected in 24 hours for some analyses. By increasing the amount of material collected on a single filter by a factor of 25 to 35, the temporal resolution could be improved at least hourly, allowing diurnal changes in the chemical composition of atmospheric aerosols to be studied.

Since the operation of the particle concentrator removes a large fraction of the matrix gas, a large volume of gas can be sampled without having to draw the entire volume through a filter. Thus, losses due to volatility are reduced.

Sampling artifacts, such as adsorption of gases by the filter media are reduced as the volume of gas drawn through the filter is reduced.

Since a large volume of gas is sampled without having to draw the entire volume through the filter, the inherent advantages of collecting this sample on a smaller sized filter will be achieved.

The invention comprises a particle concentrator comprising, in sequence, a diffuser section having an inlet and an outlet, a charging section including electrical charging means for charging particles passing through the charging section, a focussing section including electrical focussing means for focussing electrically charged particles passing therethrough and to deflect the charged particles radially inwardly towards the central axis, a convergent section having a large end connected to the focussing section and a smaller end, and a virtual impactor particle concentrator connected to the smaller end of the convergent section. The virtual impactor particle concentrator comprises a nozzle, a major discharge passage extending laterally (radially) immediately after the nozzle and a minor discharge passage extending axially after the nozzle. The minor discharge passage is larger in diameter than the nozzle. The charged particles tend to proceed along the central axis into the minor passage while carrier gas largely stripped of particulates passed into the major passage. In one embodiment, the electrical charging means for electrically charging the particles comprises a field/discharge system. In a further form of the apparatus, the field/discharge system comprises a plurality of charging cells followed by a plurality of collection cells. In a further arrangement, the apparatus includes electrical means for focussing the charged particles in the form of a plurality of ring electrodes.

There are several potential arrangements of electrodes.

ring electrodes unipolar to attract or repel charged particles paired ring electrodes with opposite potentials applied between the pair to alternately attract and repel the charged particles a central electrode to attract charged particles, paired with a conical arrangement of ring electrodes to repel the charged particles.

In yet another arrangement, the nozzle of the virtual impact concentrator comprises a circular nozzle, with the major discharge passage forming an annular passage extending around the nozzle, and including exit for means for passage of fluid largely stripped of particles from the major discharge passage. In yet another arrangement, the electrical charging means and the electrical focussing means are each of a value to deflect at least the majority of particles in a predetermined range of particle dimensions.

In a preferred arrangement, the predetermined range of particles is from 0.005 to 20 µm, with a more preferred range being from 0.01 µm to 10 µm.

A further aspect of the invention is a method of concentrating particles in a fluid flow, comprising feeding the fluid flow through a diffuser, feeding the flow from the diffuser through an electrical charging section and charging the particles in the flow, feeding the flow from the electrical charging section through an electrical focussing section and deflecting charged particles towards the central axis of the charging section, feeding the flow from the focussing section through a convergent section to a virtual impactor concentrator, deflected particles passing through a nozzle of the concentrator and discharging the flow stripped largely of particles laterally into a major discharge passage, while a concentrated stream of particulates continues axially for downstream collection and sampling.

In a further feature, the method includes electrically charging and focussing the particles to deflect at least a majority of particles in a predetermined dimensional range.

Critical to the focussing of particles prior to the flow entering the virtual impactor is the concept of a "capture tube". Fluid dynamic modelling of the new virtual impactor has shown that the particles preferably be focussed into a region within about 0.316 R where R is the radius of the throat of the virtual impactor. Any particle within this capture tube will pass through the virtual impactor and be retained in the minor flow. The value for this region may vary by 10%, but a preferred value is within 2% of the above ratio, with a still more preferred value being with 0.5% of this value.

Another important component of the virtual impactor is the shape of the channel for the major flow. Fluid dynamic modelling has shown that this channel must decrease in height as 1/r where r is the distance from the central axis of the impactor measured radially outward. This feature eliminates recirculation fo flow in the channel, improving the performance of the impactor and reducing the pumping capacity required to move the major gas flow, thus reducing cost and increasing efficiency (see FIG. 2).

In the following detailed description, various dimensions are presented. It will be understood that these dimensions are not intended to be limiting of the scope of this invention. The invention may be readily modified by scaling up or down by any amount, as well as by altering relative dimensions by up to 50% but preferably by no more than 10% and still more preferably by no more than 2% of the expressed values.

BRIEF DESCRIPTION OF THE DRAWINGS

FIGS. 8, 9 and 10 illustrate the focussing paths for three different particle sizes;

DETAILED DESCRIPTION OF THE PREFERRED EMBODIMENTS

Figure 1:
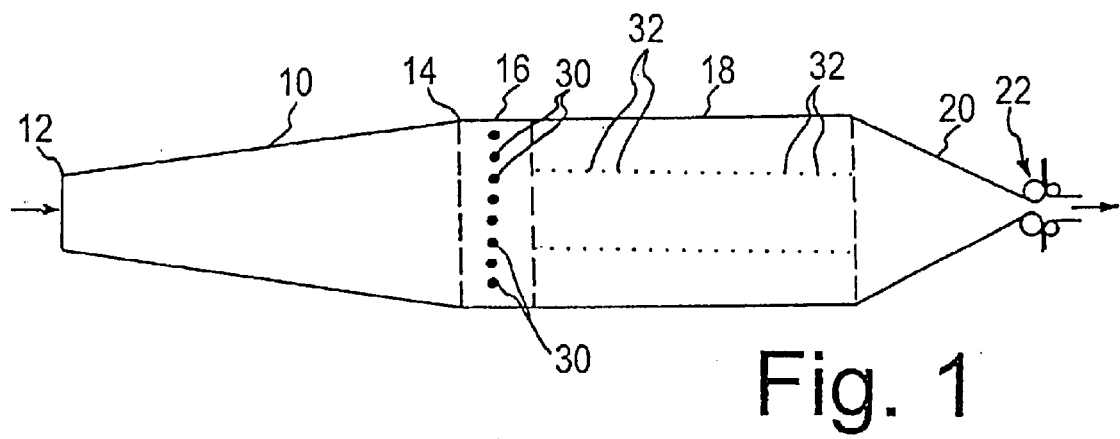
FIG. 1 is a longitudinal cross-section through one form of apparatus.
Figure 2:
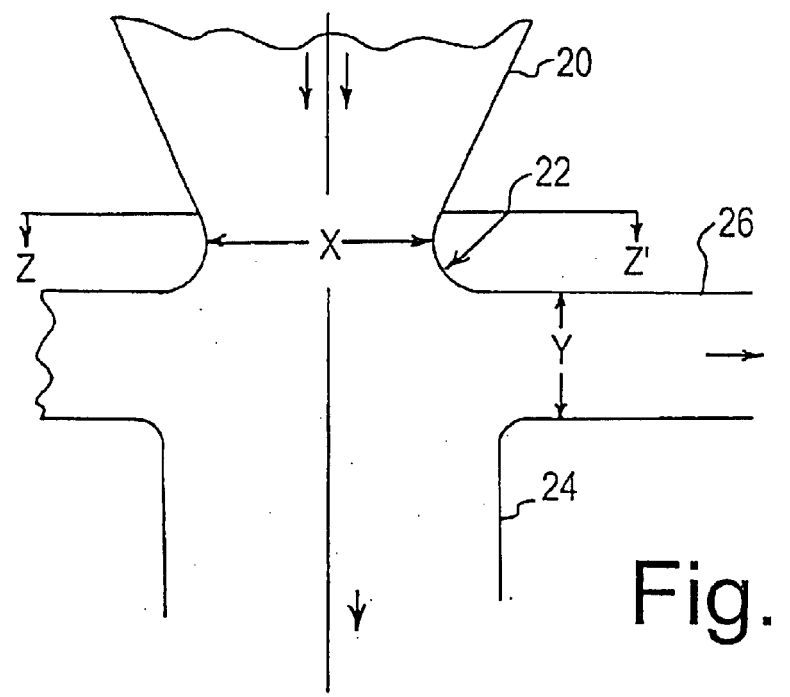
FIG. 2 is an enlarged cross-sectional view of the discharge opening of the virtual impactor of FIG. 1 to an enlarged scale.
Figure 3:
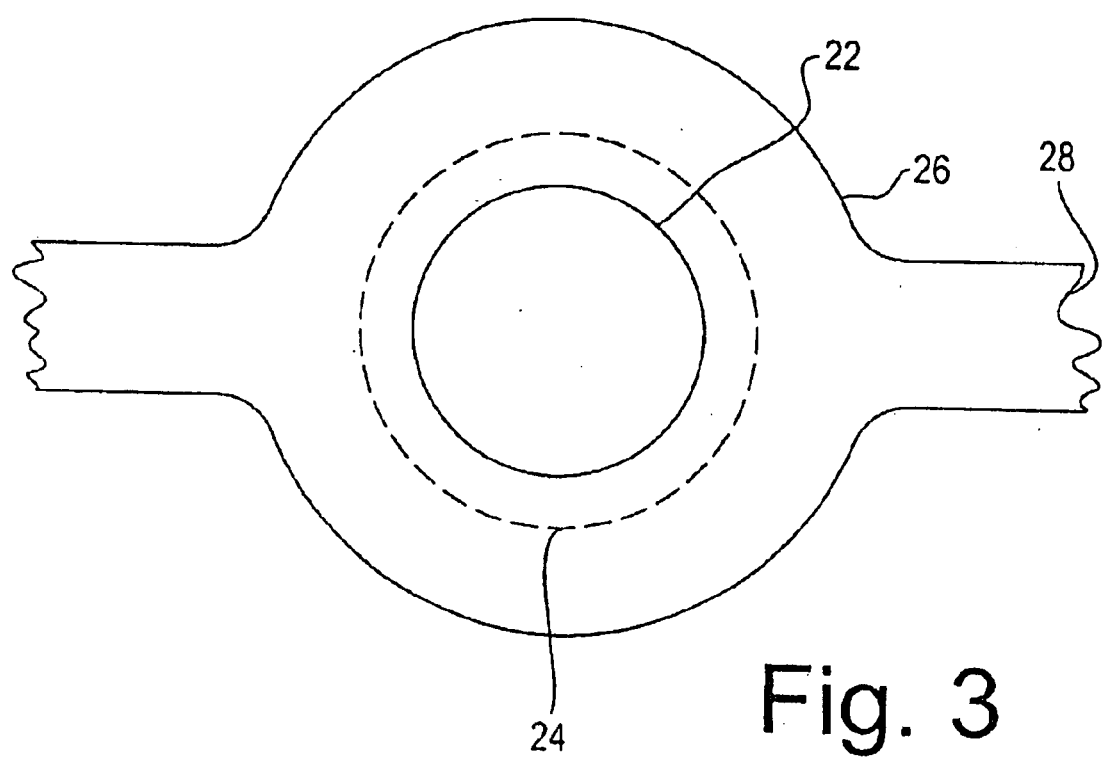
FIG. 3 is a cross-section on the line Z—Z of FIG. 2.
Figure 4:
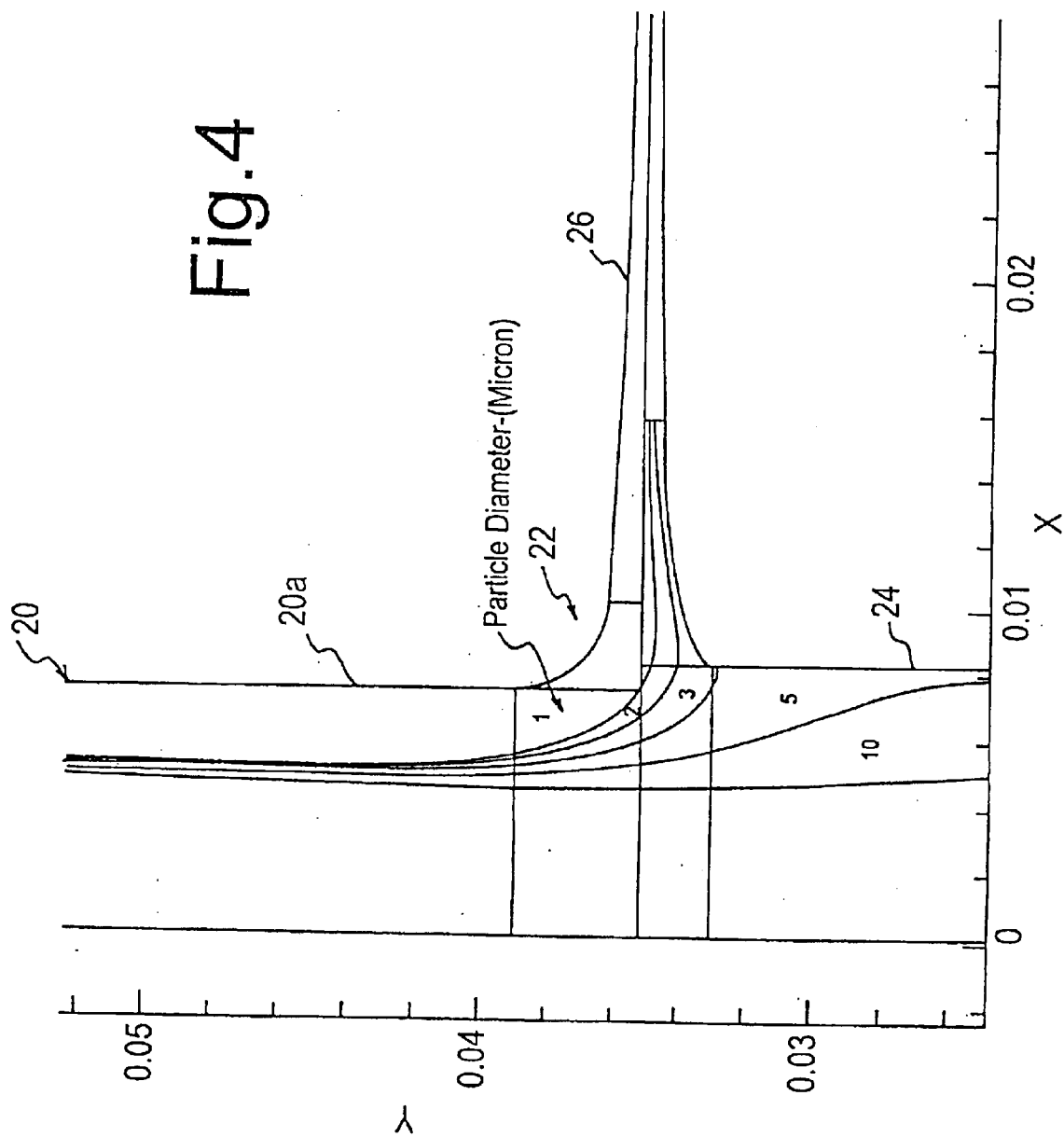
FIG. 4 is a diagrammatic cross-section, illustrating the flow pattern in a virtual impactor as in FIGS. 1 and 2.
Figure 5:
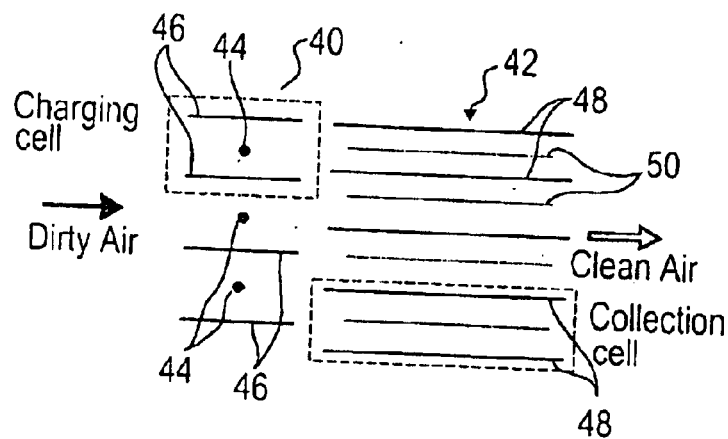
FIG. 5 illustrates diagrammatically the charging and collection cells of the charging section.
Figure 6:
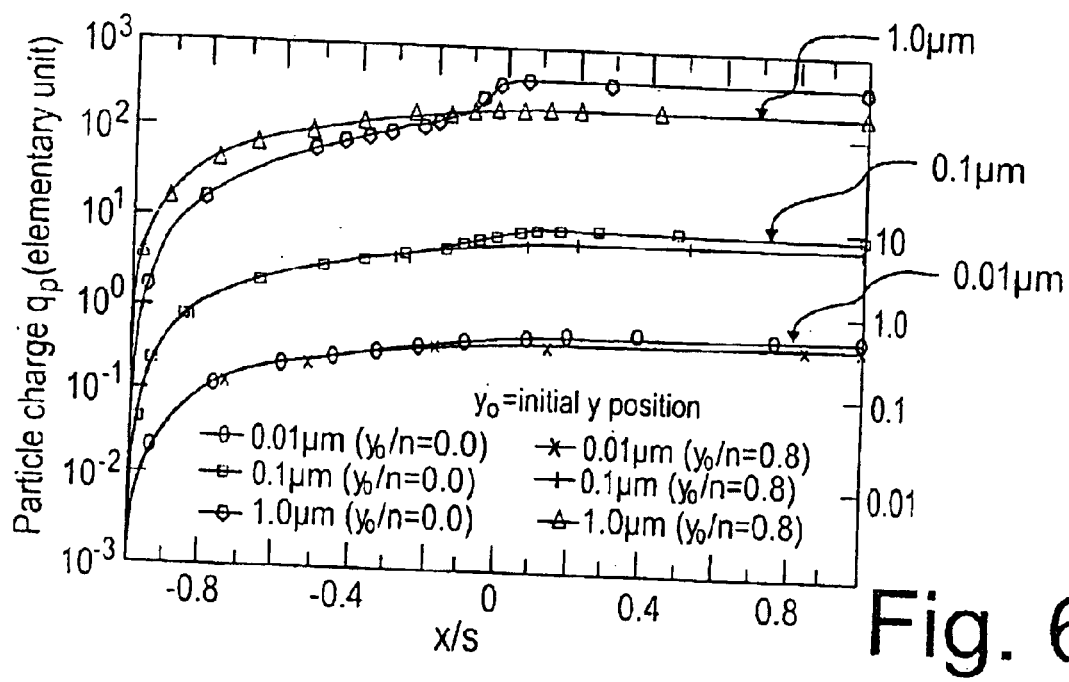
FIG. 6 illustrates charging efficiency of a typical plate cell for 3 particle sizes.
Figure 7:
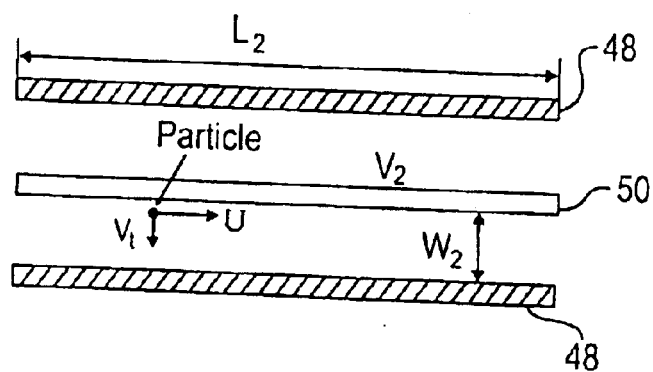
FIG. 7 illustrates the charging cells and collection cells of FIG. 5 in more detail.

As seen in FIGS. 1 and 2, one form of concentrator in accordance with the invention comprises a diffuser cone section 10 having an inlet 12 for connection to a fluid flow to be sampled. In the example the inlet 12 is approximately 5½ cm in diameter and the section 10 tapers outwardly to an exit end 14 approximately 12 cm diameter. There follows a charging section 16 and a focussing section 18. The section 18 is connected to a conical section 20 which decreases to a throat or nozzle 22 at about 1 cm diameter. The length of section 10 is about 26 cm, the length of section 16 is about 5 cm, the length of section 18 is about 21 cm and section 20 is about 12 cm long.

A minor discharge passage 24 exits axially from the nozzle 22 and an annular major discharge passage 26 exits laterally from the nozzle. The nozzle diameter as noted above is at X in FIG. 2. The diameter of the minor discharge passage 24 is about 1.125 cms. The major discharge passage 26 has a dimension Y (FIG. 2).

The dimension Y decreases radially outward from centre by $kr^{-1}$, where k is a constant.

Incoming fluid enters inlet 12 and flows through the diffuser section 10 and through the charging section 16. In the section 16 are a plurality of corona wires 30 which charge the particles in the fluid. From the charging section 16 the fluid and charged particles flow through the electrical focussing section 18. This section has a plurality of ring electrodes 32. Electrodes 32 focus the charged particles in the focussing section 18 radially inwardly to concentrate them along the centre axis. In the aerodynamic focussing section 20 the flow is accelerated until it reaches the nozzle 22. The final result is that all, or at least a very large majority, of the particles of sizes it is desired to collect or sample are sufficiently close to the central axis that they pass straight through the impactor to be collected downstream of passage 24. Excess gas flow is discharged through passage 26 and is substantially depleted of particles.

FIG. 4 is a diagrammatic illustration of some flow paths as can occur in the arrangement of FIGS. 1 and 2.

As seen in FIG. 3, an outlet 28 is provided from the major discharge passage 26 for discharge to the outside.

As seen in FIG. 1, the focussing section 18 includes an array of ring electrodes 32 (described in more detail below). These electrodes focus particles into a virtual "capture tube" having an approximate radius of 0.3 R (R=radius of impactor throat 22) along the axis where all particles within this tube transit the separator. This goal is to focus the tiny particles into this tube so that they are not lost to the major flow in the separator.

The dimensions of the various members of the impactor concentrator, or separator, that is the nozzle 22 dimensions and the sizes of the major and minor discharge passages 26 and 24, depend upon various factors but predominantly on the particular particle size or average particle size of a range which is to be collected. Thus, if the design aerodynamic particle diameter size is fixed at a value of Dp (the particle size associated with a 50% collection efficiency), the nozzle diameter can be expressed as:

$$D_o = (\text{constant}) \left( \frac{P_p D_p V_o}{S_t} \right)$$

where $D_o$ equals the dimension X in FIG. 2 and $S_t$ is the critical Stokes number and is approximately 0.75–0.79 for virtual impactors.

In FIG. 4, the focussing section 18 is shown with a short straight section 20*a* before the nozzle 22, this being a possible modification. Also in FIG. 4 the major discharge passage has a reducing dimension, as shown, to maintain a favourable pressure gradient in the passage. This arrangement in FIG. 4 illustrates paths of five particle diameters with a cut-off diameter of approximately 3 $\mu$m for the particular system.

In FIG. 4, the exiting flow boundary conditions establish a volumetric discharge of 10% in the minor discharge passage 24 and 90% in the major discharge passage 26.

Efficient charging of the particles is important and there are several mechanisms which can be employed, such as diffusion charging, field charging, ultraviolet radiation charging and radioactive source charging. The various methods often relate to a preferred particle size range wherein the particle charging is most effective. Thus, diffusion charging and field charging, or a combination thereof is most effective for particle diameters larger than 0.1 $\mu$m, but is noticeably less than 100% efficient for particles in the 0.01 $\mu$m diameter range.

In the present invention, the particle charging system is predominantly field charging. A strong electric field—10–20 $KV/cm^2$ —is used to strip electrons from aerosol particles. Because the field applied is generally strong enough for the creation of a corona discharge, diffusion charging will to a degree be present simultaneously.

The geometry of a typical charging and collecting cell unit is sketched in FIG. 5. The precipitator consists of two sets of cells or plates 40, 42 located in aerosol flow. Charging cells 40, located upstream, consist of alternating wires 44 at high DC voltage, and plates 46 at ground potential perpendicular to flow. The plate surface is aligned with the flow direction. The second set of collecting cells 42 are located immediately downstream from the charging cells 40 and consist of alternating plates at ground 48 and high voltage. The charging efficiency of a typical plate cell, as used in such precipitators, is given in FIG. 7 for three particle sizes: 1.0, 0.1 and 0.01 $\mu$m. It is seen that the charge is acquired in a region very close to high voltage wire and that the charging level decreases appreciably at the smallest particle size. In fact, the charging efficiency is noticeably less than 100% for particles as small as 0.01 $\mu$m.

FIGS. 6 and 7 illustrate diagrammatically, in more detail, the charging cells 40 and collecting cells 42 of FIG. 5.

A highly effective electrostatic focussing system is desired in view of the desired acceptable particle cut off size—with a maximum of about 1.0 $\mu$m, and in view of the difficulties associated with the charging of the smaller particles of interest—in particular in the range 0.01 $\mu$m to 0.1 $\mu$m. Thus the possibility exists of singly charged particles and charging efficiencies less than 100% in the lower particle diameter range.

A major component is the axial through-flow velocity. An additional constraint is the minimization of the fraction of concentrating aerosol particles adhering to or captured by the focussing section walls or electrodes. The velocity is limited also by the maximum field strength, which is in turn limited by the breaking/arcing limit, for example in the range $1–2\times10^6$ volts per meter.

The focussing system comprises an array of ring electrodes 32 (seen in FIG. 1) placed inside the capture tube radius, that is 31.6% of the outer wall radius. These rings are located inside the capture radius in the event that the particle sizes of interest would not have adequate radial momentum to carry them inside the capture radius if the focussing forces terminated further from the axis.

Figure 10:
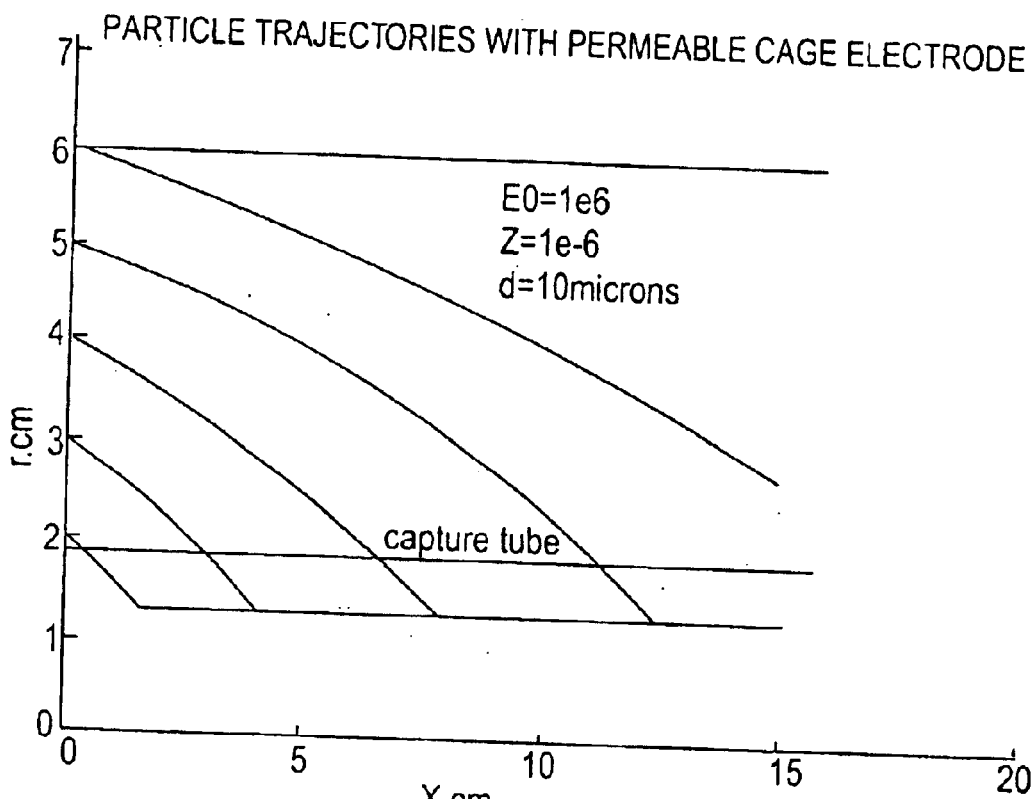

FIGS. 8, 9 and 10 relate to a duct gas velocity of 1.47 meters per second and with a field E and a mobility Z of $1\times10^6$ and $1\times10^{-6}$ respectively. E represents electric field strength used to focus particles into capture tube. Z represents the electrical mobility of the particle (i.e. how it responds when put in an electric field). To achieve the same mobility for two particles in which one is larger and one is smaller, the larger one requires more charge. These figures are for three differing particle diameters 2, 3 and 10 microns, and it will be seen that particle size has a minimal effect on the trajectories. Thus particle mobility is the dominating feature, not its mass. This is because particles so small have almost zero relaxation time.

Figure 11:
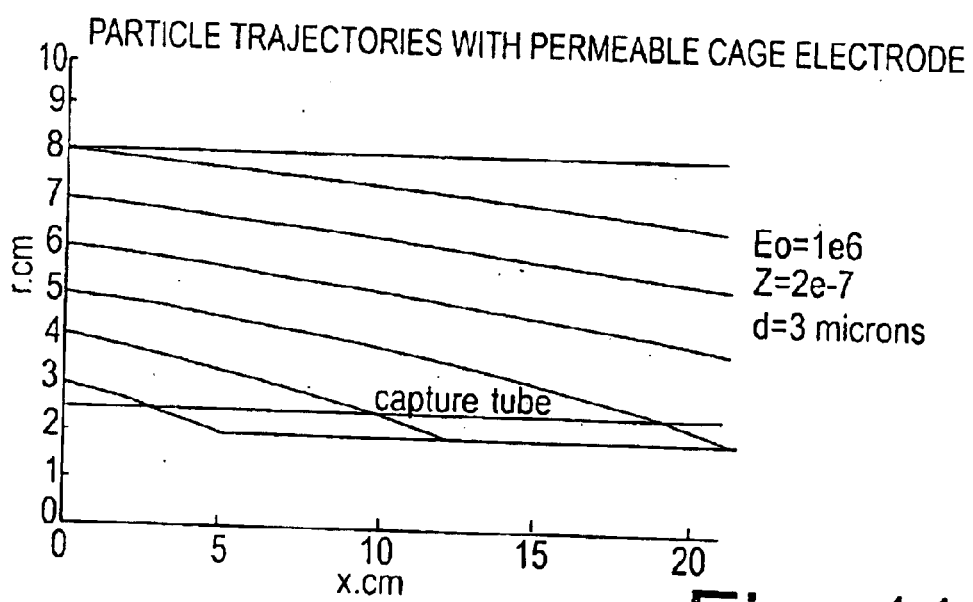
FIG. 11 illustrates the focussing path for particles with lower mobility than those of FIGS. 8, 9 and 10.

From these figures it will be seen that substantially 100% of the particles, of all sizes, would be captured in a collector of length less than 20 cms, with the stated field and velocity. FIG. 11 illustrates the effect of increasing the tube (focussing section) radius to 8 cm from 6 cm at a mobility of $2\times10^7$. The flow of velocity is reduced to 0.83 meters per second, with the same section length of 21 cms. The collection rate is about 44%.

The invention as described above and illustrated in the drawings, is particularly intended for the sampling of exhaust gases of the vehicle and other engines. The apparatus as illustrated in FIG. 1 is dimensioned to match with the normal probe tube located in the exhaust stream, sampling at a rate of 1000 liters per minute, with an internal flow area of 23.76 cm$^2$ and associated diameter of 5.5 cm. The sampled gas stream must be decelerated from the sampling probe velocity, for example 7 meters per second, to a velocity in the order of 1–2 meters per second prior to the electrostatic focussing.

For other purposes, the dimensions of the various parts of the apparatus, and the operating parameters, can vary. Also, the desired particle size range to be concentrated will impose some dimensional variations. Once concentrated, the flow is directed to any desired form of collecting and/or measuring device for the obtaining of actual proportions of the particles.

It is also possible to form a multiple stage concentration apparatus by feeding the output in the minor discharge passage into a further concentration system comprising a diffuser cone (if necessary), may not be necessary in subsequent stages focussing section and virtual impactor or nozzle. Optionally, an additional charging section is provided, if required, in advance of the focussing section.

Depending upon the particular form of collecting and/or measuring device used, some level of vacuum may be applied at the outlet end of the major discharge passage.

The arrangement of electrodes required for focussing the charged particles can take several forms depending on performance criteria (e.g. flow rate, acceptable losses, initial particle concentration, etc.)

Figure 12:
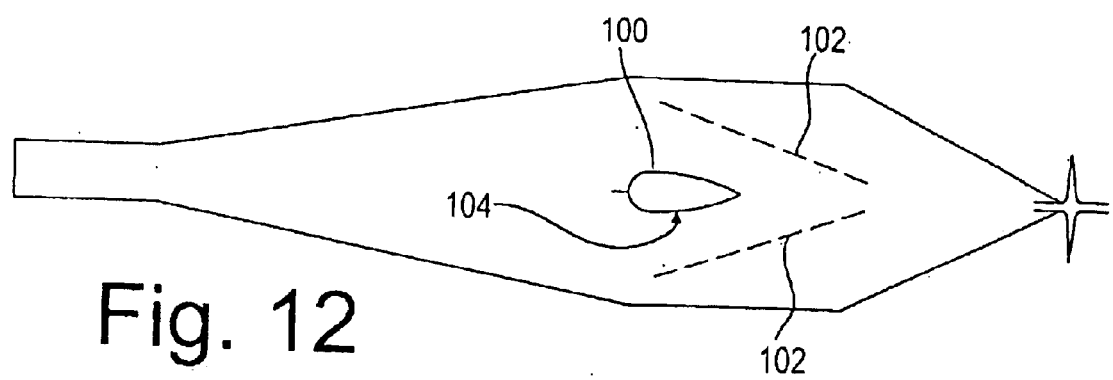
FIG. 12 is a further version of the device.
Figure 13:
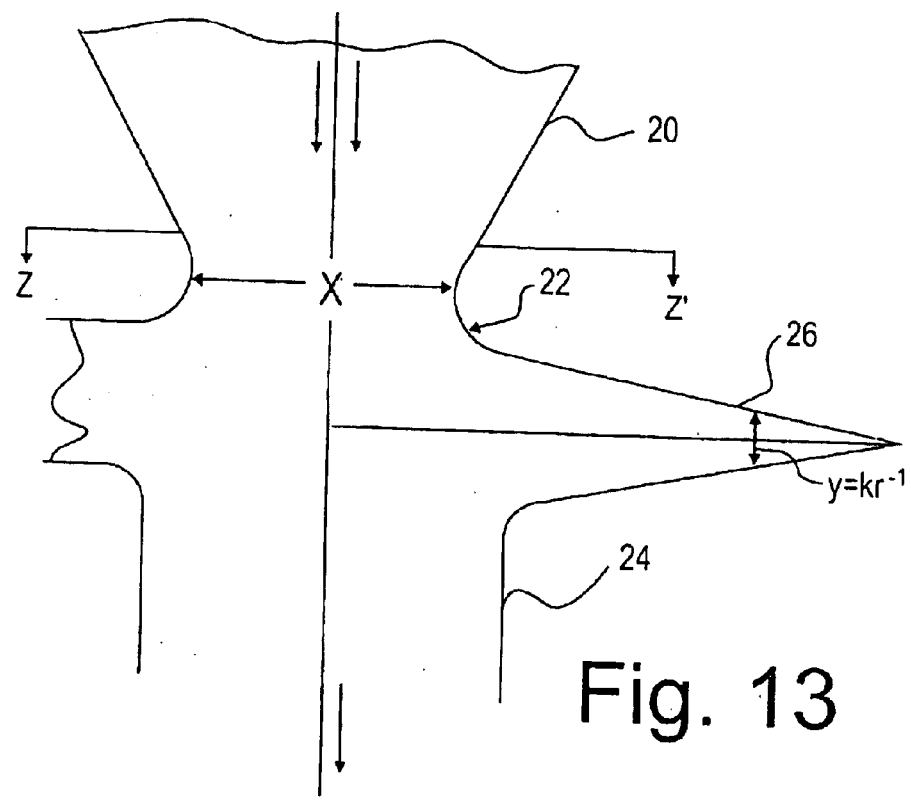
FIG. 13 is a view as in FIG. 2, illustrating the further embodiment of FIG. 12.

FIGS. 12 and 13 illustrate an arrangement of the invention that minimizes particle loss. In this version, a central electrode 100 with attracting potential applied, is shaped as an aerodynamic fairing so as to produce minimal disturbance to the gas flow. This electrode is located along the axis of the focussing section. This electrode has accompanying it a screen electrode 102 with repelling potential applied and shaped in a converging cone. The central electrode may be designed in such a way that a corona discharge wire may be incorporated into the upstream, widest end of the electrode thus combining the charging and focussing features of the concentrator. To further minimize particle loss by attraction to the electrode, a sheath gas flow may be introduced along the surface of this fairing electrode to prevent particles from contacting the surface 104, and to sweep particles that approach into the flow inside the "capture tube".

The present invention, although described by reference to particular embodiments, has a scope which embraces the claims which accompany this specification.

What is claimed is:

1. A particle concentrator for concentrating particles carried by a carrier gas comprising, in sequence, a diffuser section having an inlet and an outlet end;

a charging section including electrical charging means for charging particles passing therethrough;

focussing section having a central axis and including electrical focussing means for focussing electrically charged particles passing therethrough towards said central axis;

a convergent section having a large end connected to said focussing section and a smaller end; and a virtual impact particle concentrator connected to said smaller end, said virtual impact particle concentrator comprising a nozzle, a major discharge passage extending laterally immediately after said nozzle for discharging carrier gas generally depleted of particles and a minor discharge passage extending axially after said nozzle for discharging an enriched particle stream, said minor discharge passage of a dimension larger than said nozzle.

2. An apparatus as claimed in claim 1, wherein said electrical means for electrically charging said particles comprises a field/discharge system.

3. An apparatus as claimed in claim 2, said field/discharge system comprising a plurality of charging cells followed by a plurality of collection cells.

4. An apparatus as claimed in claim 1, said electrical means for focussing said charged particles comprising a plurality of ring electrodes to form a virtual capture tube.

5. An apparatus as claimed in claim 1, said nozzle comprising a circular nozzle, and said major discharge passage comprising an annular passage extending around said nozzle; and including exit means for passage of a stream depleted of particles from said major discharge passage.

6. An apparatus as claimed in claim 1, said electrical charging means and said electrical focussing each at a value to deflect at least the majority of particles in a predetermined range at particle dimensions.

7. An apparatus as claimed in claim 6, said predetermined range being 0.01 $\mu$m to 10.0 $\mu$m.

8. An apparatus as claimed in claim 1, said major discharge passage decreasing in diameter away from said central axis.

9. An apparatus as defined in claim 8, wherein said major discharge passage is annular.

10. An apparatus as claimed in claim 1, wherein the dimensions of components are defined as:

$$D_o = (\text{constant}) \left( \frac{P_p D_p V_o}{S_t} \right)$$

Wherein

| | |
|---|---|
| $D_o =$ | diameter of accelerating nozzle throat |
| $V_o =$ | accelerating nozzle throat velocity |
| $S_t =$ | stokes number |
| $D_p =$ | a selected particle size (diameter) |
| $P_p =$ | particle density. |

11. A method of concentrating particles in a fluid flow, comprising:

feeding said flow through a diffuser;

feeding said flow from said diffuser through an electrical charging section
and charging particles in said flow;

feeding said flow from said electrical charging section through an electrical focussing section and focussing charged particles towards a central axis;

feeding flow into a impactor concentrator;

discharging a particle-depleted major flow radially through a major discharge passage of said virtual impactor concentrator; and, discharging a particle-enriched minor flow axially through a minor discharge passage.

12. The method of claim 11, including electrically charging and focussing said particles to focus at least a majority of particles in a predetermined dimensional range.

13. The method of claim 12, said charging and focussing particles in the range of 0.01 μm to 1.0 μm and concentrating said focussed particles in said virtual impact concentrator.

* * * * *